US00PP21586P3

(12) United States Plant Patent
Tristram

(10) Patent No.: US PP21,586 P3
(45) Date of Patent: Dec. 21, 2010

(54) ***AJUGA* PLANT NAMED 'BINSUGPLU'**

(50) Latin Name: *Ajuga reptans*
Varietal Denomination: BINSUGPLU

(76) Inventor: Mike Tristram, Binsted, Arundel, West Sussex (GB) BN18 0LL ( * ) Notice: Subject to any disclaimer, the term of this patent is extended or adjusted under 35 U.S.C. 154(b) by 12 days.

(21) Appl. No.: 12/459,403

(22) Filed: Jun. 30, 2009

(65) Prior Publication Data

US 2010/0005554 P1 Jan. 7, 2010

(51) Int. Cl.
*A01H 5/00* (2006.01)

(52) U.S. Cl. ..... Plt./401

(58) Field of Classification Search ..... Plt./263, Plt./401

See application file for complete search history.

*Primary Examiner*—Susan B McCormick Ewoldt

(57) ABSTRACT

A new and distinct cultivar of *Ajuga* plant named 'BINSUGPLU' which exhibits a compact mat-forming habit comprised of short internodes and contrasting foliage as between the deep pink to purple color of the newly emerged leaves and the gray-green color of the mature leaves. In addition, the leaves of 'BINSUGPLU' are rounded and thick, and exhibit a slight pewter-like metallic sheen. In combination, these traits set 'BINSUGPLU' apart from all other existing varieties of *Ajuga* known to the inventor.

2 Drawing Sheets

Genus: *Ajuga.*
Species: *reptans.*
Denomination: 'BINSUGPLU'.

BACKGROUND OF THE INVENTION

This application claims the benefit of priority under 35 U.S.C. 119(f) of the application for a grant of European Community Plant Breeders Rights which was filed for the instant plant variety on Jul. 7, 2008, Application Number 2008/1554.

The present invention relates to a new variety of bugle grown for use in container, rock garden, and as a small-scale groundcover for the landscape. The new invention from the family Labiateae is known botanically as *Ajuga reptans* and will be referred to hereinafter as 'BINSUGPLU'.

The new *Ajuga* cultivar named 'BINSUGPLU' has resulted from a breeding program established at the inventor's nursery in West Sussex, United Kingdom, in 2004. The aim of the breeding program is to produce new and improved varieties of *Ajuga* which are robust in cultivation and colorful in the landscape. In particular, the inventor wished to develop new varieties which are consistent with the robust qualities of the inventor's *Ajuga* varieties, *Ajuga* 'Black Scallop' (U.S. Plant Pat. No. 15,815) and *Ajuga* 'BINPARCOL' (U.S. Plant Pat. No. 20,293). The criteria for selection include foliage interest through pronounced and contrasting leaf coloration, and broader, glossier and thicker leaves which confer robustness, tolerance to high temperatures and light intensity, and resistance to powdery mildew attack.

'BINSUGPLU' was selected by the inventor in 2006 from a variable population of vegetatively propagated plants of *Ajuga* 'Burgundy Glow' (unpatented). 'Burgundy Glow' is a variegated variety which, due to its variegation, does not reproduce entirely true to type when asexually reproduced, especially using tissue culture. Initially, seven unique tissue culture explant clones of potential were isolated and subjected to subsequent vegetative propagation and growing on in a range of container sizes, for repeated evaluation of overall appearance, robustness, distinctness, and uniformity. From these growing trials, 'BINSUGPLU' was selected for its ability to form a vigorous carpet of robust foliage, together with a more intense deep pink to purple coloration to the newly emerged foliage. In addition, 'BINSUGPLU' grows with a constantly creeping and branching habit, its stems and branches have short internodes and growth extends by approximately 6-9 inches per year.

'BINSUGPLU' exhibits compact, mat-forming habit, large, glossy, thick multi-colored leaves, and mid-blue flowers that bloom in late summer. Cultural needs include full sun, moisture retentive soil, and moderate water. 'BINSUGPLU' exhibits resistance to powdery mildew, and is hardy to USDA Zone 3.

The degree of contrast in foliage coloration is considered by the inventor to be unique to this variety. Newly-emerged leaves are deep pink to purple in color, especially under conditions of full sun and cool nights. Mature leaves are predominantly grey-green in color, with occasional evenly distributed flecks of cream-white. Overall, the foliage carpet is bright with a slight pewter-like metallic sheen. The leaves of 'BINSUGPLU' are distinctly more round and thicker than other varieties of *Ajuga* known to the inventor, other than the inventor's previous releases which share this characteristic.

'BINSUGPLU' is distinguishable from all other *Ajuga* known to the inventor. The closest comparison plant is the parent plant *Ajuga* 'Burgundy Glow' (unpatented). The new variety 'BINSUGPLU' is distinguishable from 'Burgundy Glow' by larger, round, thicker leaves, and brighter foliage color with prominent contrasting foliage colors, between deep pink to purple in the newly emerging leaves and grey-green in the mature leaves.

The first asexual reproduction of 'BINSUGPLU' occurred in 2006 and was accomplished at the inventor's nursery in West Sussex, United Kingdom. Asexual propagation was carried out by the inventor using the method of stem cuttings. Since that time under careful observation 'BINSUGPLU' has been determined fixed, stable and true to type in subsequent generations of asexual propagation.

SUMMARY OF THE INVENTION

The following traits have been repeatedly observed and represent the distinguishing characteristics of the new *Ajuga* cultivar named 'BINSUGPLU'. These traits in combination distinguish 'BINSUGPLU' from all other existing varieties of *Ajuga* known to the inventor. 'BINSUGPLU' has not been tested under all possible conditions. Phenotypic differences may be observed with variations in environmental, climatic, and cultural conditions without however any variance in genotype.

1. 'BINSUGPLU' exhibits compact mat-forming habit.
2. The stems and branches of 'BINSUGPLU' are comprised of short internodes and the rate of stem growth is approximately 6 inches per year.
3. 'BINSUGPLU' reaches a maximum height of 200 mm.
4. 'BINSUGPLU' exhibits contrasting foliage, between deep pink to purple color of the newly emerged leaves and gray-green color of the mature leaves.
5. The leaves of 'BINSUGPLU' are rounded and thick, and exhibit a slight pewter-like metallic sheen.
6. 'BINSUGPLU' exhibits mid-blue flowers which bloom in late summer.
7. 'BINSUGPLU' is hardy to USDA Zone 3.

BRIEF DESCRIPTION OF THE DRAWINGS

The accompanying color drawings illustrate the overall appearance of the new *Ajuga* cultivar named 'BINSUGPLU' showing color as true as is reasonably possible to obtain in color reproductions of this type. Color in the drawings may differ from color values cited in the detailed botanical description, which accurately describe the actual color of the new variety 'BINSUGPLU'.

The drawing labeled

The drawing labeled

Figure 1:
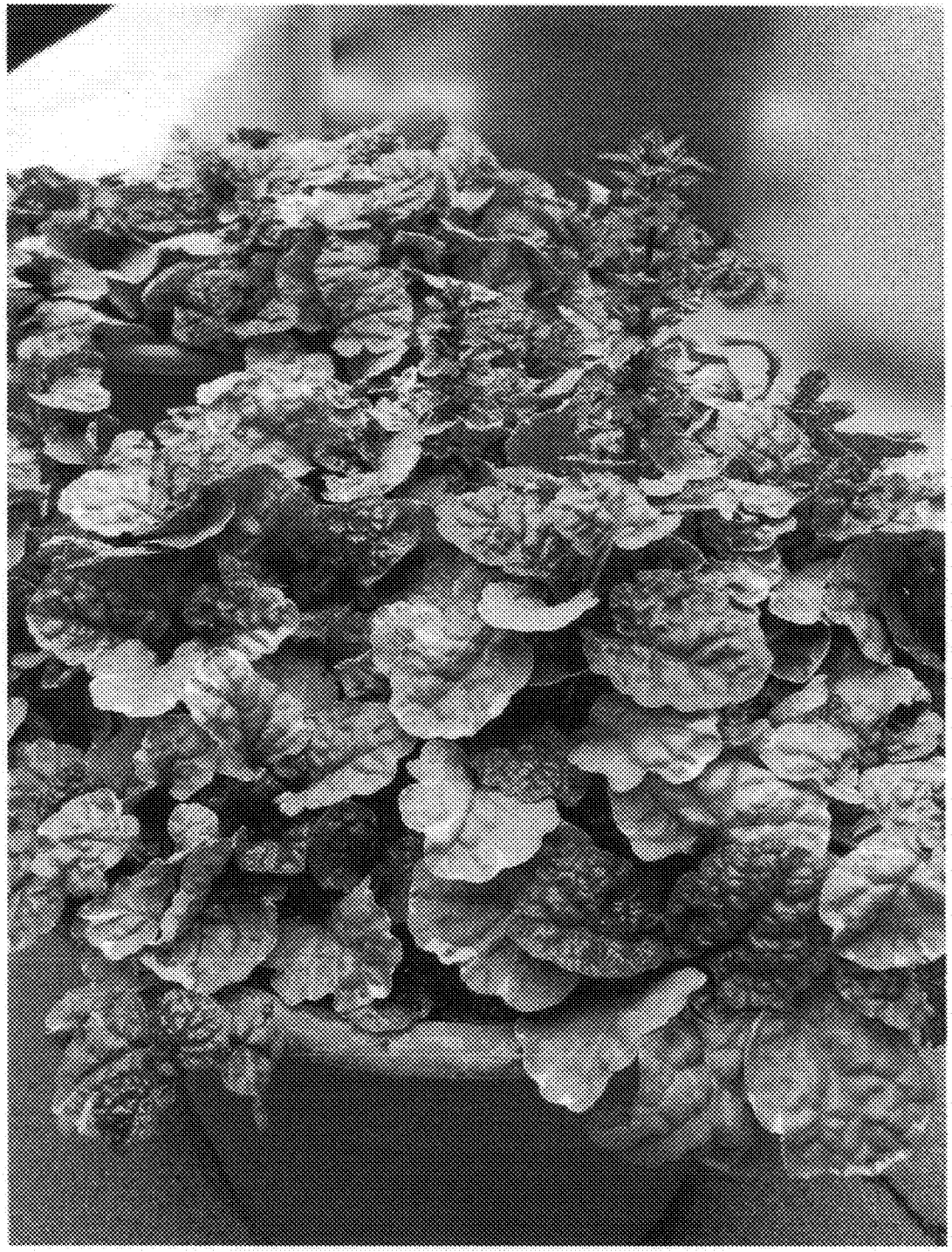
FIG. 1 depicts a single plant, approximately fifteen months old, which has been growing out of doors in West Sussex, United Kingdom. The illustrated plant is growing in a 20 cm diameter container and has branched so completely that the new growth is pushing through the older growth, beginning to form a mound of foliage. If the plant is unrestricted then it will grow and spread as a flat carpet. This drawing also illustrates the mid-blue flower spike of 'BINSUGPLU'.
Figure 2:
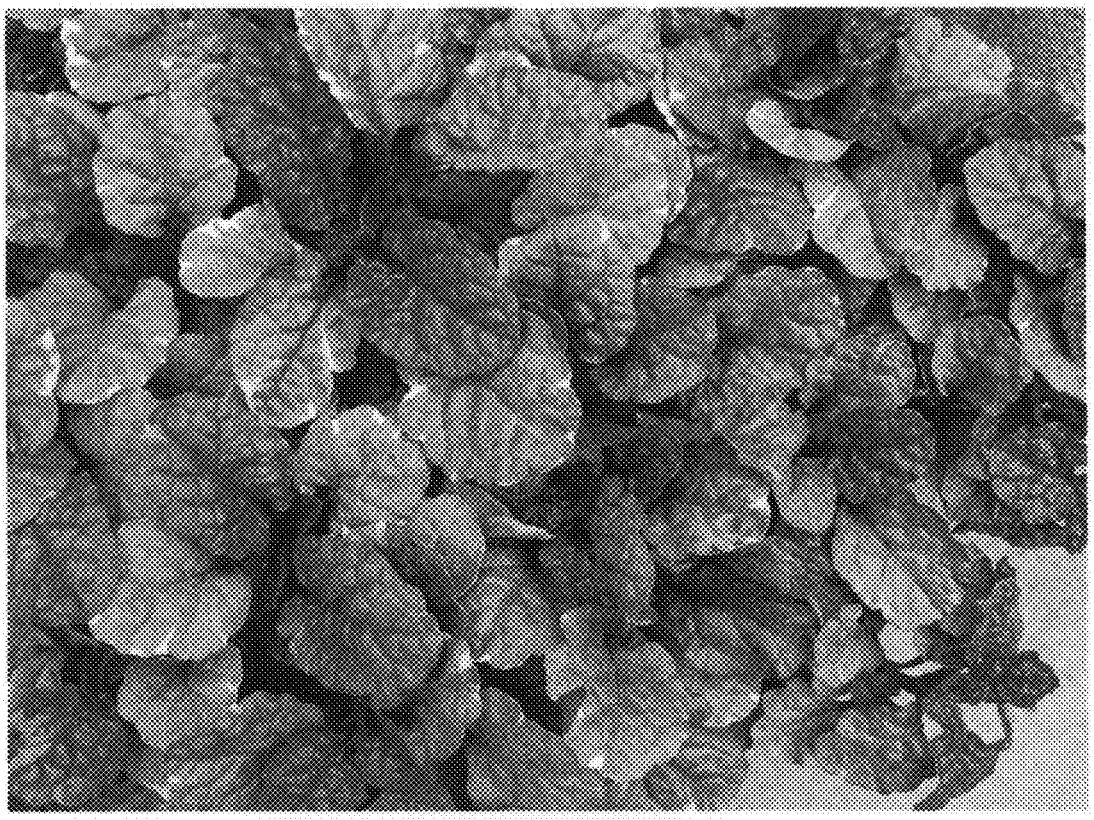
FIG. 2 depicts a close-up view of the plant shown in FIG. 1. This drawing illustrates the contrasting coloration of the foliage, between deep pink to purple of the newly emerged leaves and the grey-green color of the mature leaves. The occasional white marginal flecking is also evident in this drawing.

Both drawings were made using conventional techniques and although flower and foliage color may appear different from actual color due to light reflectance, they are as accurate as possible by conventional photography.

BOTANICAL DESCRIPTION OF THE PLANT

The following is a detailed botanical description of the new *Ajuga* cultivar named 'BINSUGPLU'. Observations, measurements, values and comparisons were collected in Santa Barbara, Calif., from 9-month-old plants growing out of doors in 1-liter containers. Color determinations are made in accordance with The 2007 Royal Horticultural Society Colour Chart from London, England, except where general color terms of ordinary dictionary significance are used. The growing requirements of the new variety 'BINSUGPLU' are similar to the species.

Botanical classification: *Ajuga reptans* 'BINSUGPLU'.
Family: Labiateae.
Genus: *AJUGA*.
Species: *Reptans*.
Denomination: 'BINSUGPLU'.
Common name: Bugle.
Habit: Compact mat-forming.
Commercial category: Perennial herb.
Use: Container, rock garden, and small-scale groundcover for the landscape.
Suggested commercial container size: 1-liter container.
Parentage: *Ajuga reptans* 'BINSUGPLU' is a clonal selection resulting from a formal breeding program. The sole parent is *Ajuga* 'Burgundy Glow' (unpatented).
Propagation method: Methods of tip cuttings, and division.
Rooting system: Fine.
Vigor (range): Low to moderate.
Crop time (range): 9-12 months to produce a 1-liter container from stem cuttings.
Temperature (range): The recommended air temperature is 20-21° Centigrade.
Plant dimensions (at maturity): A maximum of 200 mm. in height and creeping to an indefinite width.
Cultural requirements: Grow in moisture retentive soil, full sun, with moderate water.
Pest or disease resistance: Resistant to mildew.
Hardiness: USDA Zone 3.
Stem:
- *Shape.*—Cylindrical.
- *Surface.*—Glabrous.
- *Color.*—146C.
- *Stem length* (*average*).—10 cm.
- *Stem diameter* (*average*).—3 mm.
- *Internode* (*average*).—1.40 cm.

Foliage:
- *Type.*—Evergreen.
- *Leaf arrangement.*—Opposite.
- *Leaf division.*—Simple.
- *Leaf margin* (*range*).—Crenate.
- *Leaf surface* (*abaxial*).—Puberulent and rugose.
- *Leaf surface* (*adaxial*).—Glabrous and rugose.
- *Leaf appearance.*—Glossy.
- *Leaf shape.*—Reniform.
- *Leaf length* (*average*).—3.50 cm.
- *Leaf width* (*average*).—4 cm.
- *Leaf color* (*newly emerging and emerged, adaxial surface*).—Predominantly 64A, with 61A and 61B towards base of leaf.
- *Leaf color* (*newly emerging and emerged, abaxial surface*).—Predominantly in the range 138B to 191B, with infused 64B appearing as a margin approximately 2 mm-3 mm in width.
- *Leaf color* (*mature, both surfaces*).—191B with marginal flecks ranging between white and yellow-white, 158C. 182C, N138C and 161D are all individually present.
- *Leaf apex.*—Obtuse.
- *Leaf base.*—Cordate.
- *Venation.*—Pinnate.
- *Vein color* (*abaxial and adaxial surfaces*).—N138B.
- *Attachment* (*range*).—Petiolate to clasping.
- *Petiole shape.*—Sulcate.
- *Petiole surface.*—Glabrous.
- *Petiole color.*—N138B.

*Petiole dimensions.*—0.60 cm. in length and 0.25 cm. in width.

*Leaf fragrance.*—Scented when bruised.

Inflorescence:

*Inflorescence.*—Spike.

*Inflorescence dimensions.*—3.50 cm. in length and 2.50 cm in width.

*Flower quantity* (*range*).—10-14 per inflorescence.

*Bract* (*average*).—16 per inflorescence.

*Bract arrangement.*—Whorled.

*Bract attachment.*—Sessile.

*Bract shape* (*range*).—Ovate to reniform.

*Bract apex.*—Acute.

*Bract margin.*—Entire.

*Peduncle shape.*—Tetragonal.

*Peduncle surface.*—Villous.

*Peduncle strength.*—Strong.

*Peduncle color.*—N187B.

*Peduncle dimensions* (*average*).—3.25 cm. in height and 4 mm. in width.

*Bud shape.*—Globose.

*Bud color.*—94A.

*Bud surface.*—Villous.

*Bud dimensions.*—2.50 mm. in length and 2.50 mm. in width.

*Flower shape.*—Tubular.

*Flower color* (*ventral and dorsal surface*).—94A, 94B, 94C, 94D are all individually present.

*Flower dimensions.*—9 mm. in depth and 7 mm. in width.

*Flower surface* (*dorsal*).—Villous.

*Corolla tube depth.*—7 mm.

*Corolla tube width.*—2.75 mm.

*Lips.*—3 in number. Lip color (adaxial and abaxial surfaces): 94A, 94B, 94C, 94D are all individually present. Lip margin: Entire. Lip surface (abaxial): Villous. Lip apex (range): Rounded to emarginate.

*Calyx shape.*—Tubular.

*Calyx surface* (*dorsal*).—Villous.

*Sepals.*—5 in number.

*Sepals fused or unfused.*—Fused.

*Sepal color.*—189B.

*Sepal margin.*—Entire.

*Sepal apex.*—Acute.

*Sepal surface* (*abaxial*).—Villous.

*Inflorescence fragrance.*—None observed.

Reproductive organs:

*Stamen quantity.*—4 in number.

*Stamen length.*—7 mm.

*Stamen color.*—155A.

*Anther color.*—N186A.

*Anther length.*—<1 mm.

*Pollen amount.*—Low.

*Pollen color.*—162A.

*Pistil quantity.*—1 in number.

*Pistil length.*—9 mm.

*Pistil color.*—155A.

*Ovary position.*—Superior.

*Ovary shape.*—Globose.

*Ovary dimensions.*—1 mm. in height and 1 mm. in diameter.

*Ovary color.*—144A.

The invention claimed is:

1. A new and distinct cultivar of *Ajuga* plant named 'BINSUGPLU' as described and illustrated herein.

* * * * *